US008176788B2

(12) United States Patent
Tapia et al.

(10) Patent No.: US 8,176,788 B2
(45) Date of Patent: May 15, 2012

(54) SYSTEM AND METHOD OF ULTRASONIC INSPECTION

(75) Inventors: William J. Tapia, Graham, WA (US); Gary E. Georgeson, Federal Way, WA (US); Michael D. Fogarty, Auburn, WA (US); David W. Anderson, Kent, WA (US)

(73) Assignee: The Boeing Company, Chicago, IL (US)

( * ) Notice: Subject to any disclaimer, the term of this patent is extended or adjusted under 35 U.S.C. 154(b) by 610 days.

(21) Appl. No.: 12/330,125

(22) Filed: Dec. 8, 2008

(65) Prior Publication Data

US 2010/0139404 A1    Jun. 10, 2010

(51) Int. Cl.
*G01N 29/04* (2006.01)
(52) U.S. Cl. ............................................ 73/628; 73/629
(58) Field of Classification Search .................... 73/628, 73/629, 606, 611, 627, 644
See application file for complete search history.

(56) References Cited

U.S. PATENT DOCUMENTS

| | | | | |
|---|---|---|---|---|
| 2,803,128 A * | 8/1957 | Petermann | | 73/606 |
| 3,933,026 A * | 1/1976 | Ham et al. | | 73/1.86 |
| 3,996,792 A * | 12/1976 | Kubota et al. | | 73/611 |
| 4,202,216 A * | 5/1980 | Bull et al. | | 73/639 |
| 4,854,993 A * | 8/1989 | Celia | | 156/219 |
| 5,698,787 A * | 12/1997 | Parzuchowski et al. | | 73/643 |
| 6,431,002 B1 | 8/2002 | Aijima | | |
| 6,467,331 B1 * | 10/2002 | Kline-Schoder et al. | | 73/19.03 |
| 6,554,003 B1 * | 4/2003 | Birang et al. | | 134/1.3 |
| 6,848,312 B2 * | 2/2005 | Georgeson | | 73/627 |
| 7,086,285 B2 | 8/2006 | Reed | | |
| 7,131,333 B2 * | 11/2006 | Busch | | 73/620 |
| 7,141,917 B2 * | 11/2006 | Beck et al. | | 310/334 |
| 7,181,969 B2 * | 2/2007 | Busch et al. | | 73/618 |
| 7,488,270 B2 * | 2/2009 | Harada et al. | | 476/73 |

FOREIGN PATENT DOCUMENTS

EP         1 096 253 A2      5/2001

* cited by examiner

*Primary Examiner* — J M Saint Surin
(74) *Attorney, Agent, or Firm* — Klintworth & Rozenblat IP LLC

(57) ABSTRACT

An ultrasonic inspection apparatus may include a chamber partly filled with water from a first portion of the chamber to a water-line disposed apart from a second portion of the chamber, and at least one transducer disposed apart from the water-line. The at least one transducer may emit ultrasonic signals through a portion of a part being inspected towards the water-line. The water-line may reflect the ultrasonic signals emitted from the at least one transducer off the water-line, back through a portion of a part being inspected, and back to the at least one transducer. In such manner, one or more portions of a complex-shaped part may be inspected.

28 Claims, 3 Drawing Sheets

SYSTEM AND METHOD OF ULTRASONIC INSPECTION

FIELD OF THE DISCLOSURE

The disclosure relates to systems and methods for ultrasonic inspection of parts.

BACKGROUND OF THE DISCLOSURE

It is often necessary to non-destructively inspect the condition of parts which may have complex shapes. One such part which may need to be inspected may comprise a floor beam having separate caps adhered to opposing flanges which are welded to a web to create an I-beam. It may be necessary to inspect the condition of the bond-lines between the caps and the flanges of the I-beam. One conventional method of inspecting parts is pulse-echo ultrasound. However, the difficulty with verifying bond quality using pulse-echo ultrasound is that the thin gauge of the cap material and the thickness of the adhesive layer may create an interface that is virtually impossible to resolve. The peaks in an A-scan representing reflections off the back of the first bond interface and the back of the cap may not be easily discriminated. The problem may be compounded by a variance in the thickness of the adhesive layer that may prevent accurate time-based instrument gating to be utilized. Another conventional method of inspecting parts is through ultrasound. Through ultrasound is often used when inspecting bonded structure during manufacturing, with a loss of signal amplitude used to find bondline anomalies. However, the geometry of an I-beam part may prevent the region of the flanges near the web to be inspected, because it may be difficult to use an inside transducer which does not run into the web. Since this region is generally the most critical portion of the flange, traditional through ultrasound may not be a good solution. Still another conventional inspection method of inspecting parts is reflector plate pulse-echo ultrasonic testing. A target may be placed behind the test specimen where the ultrasonic signal is sent through the specimen, reflected off the target, and sent back through the specimen to be received at the transducer. The amplitude of the reflected signal may then be analyzed to determine the quality of the specimen. However, in the case of a complex part such as an I-beam, the complex geometry of the web may require part specific tooling to be produced in order to implement the reflector plate method. This approach may be costly and inefficient to implement.

An ultrasonic inspection apparatus and method is needed to reduce and/or solve one or more problems of the conventional ultrasonic inspection apparatus and/or methods.

SUMMARY OF THE DISCLOSURE

In one aspect of the disclosure, an ultrasonic inspection apparatus may include a chamber partly filled with water from a first portion of the chamber to a water-line disposed apart from a second portion of the chamber, and at least one transducer disposed apart from the water-line. The at least one transducer may be adapted to emit ultrasonic signals through a portion of a part being inspected towards the water-line. The water-line may be adapted to reflect the ultrasonic signals emitted from the at least one transducer off the water-line, back through a portion of a part being inspected, and back to the at least one transducer.

In another aspect of the disclosure, a method for inspecting a part is disclosed. In one step, a chamber may be partly filled with water from a first portion of the chamber to a water-line disposed apart from a second portion of the chamber. In another step, a portion of a part to be inspected may be disposed within the water within the chamber. In still another step, ultrasonic signals may be emitted from at least one transducer through the portion of the part being inspected towards the water-line. In an additional step, the emitted ultrasonic signals may be reflected off the water-line, back through the portion of the part being inspected, back to the at least one transducer.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
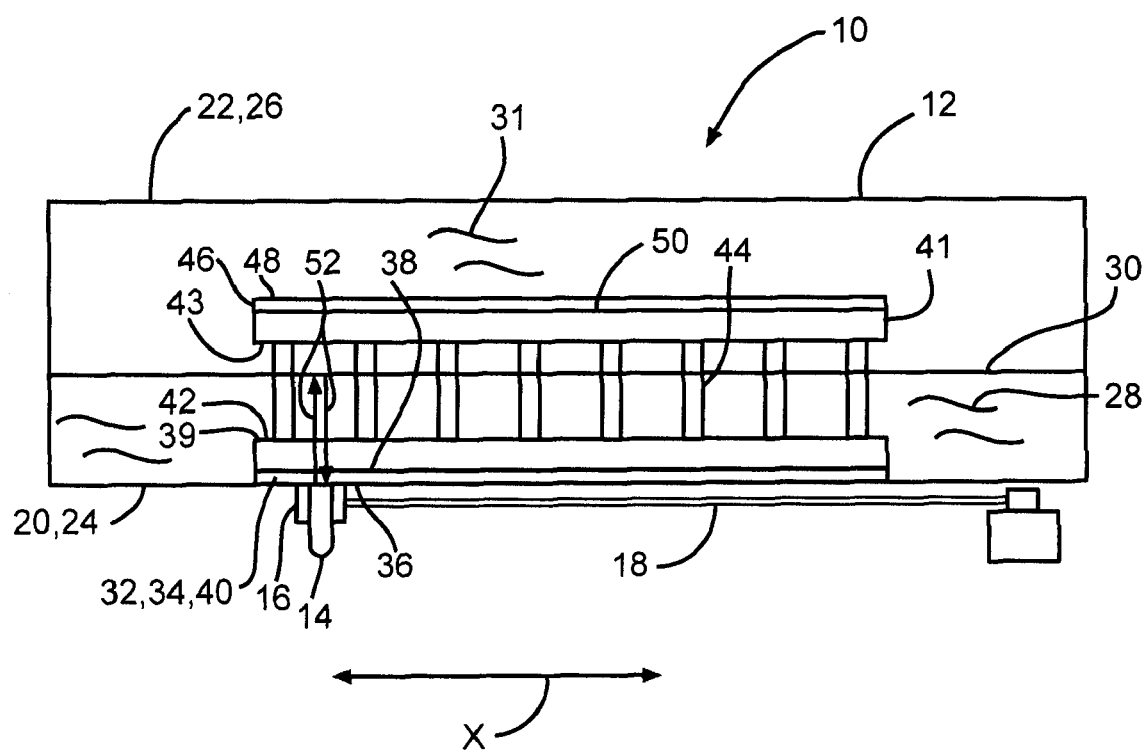
FIG. 1 is a front view of one embodiment of an ultrasonic inspection apparatus.
Figure 1:
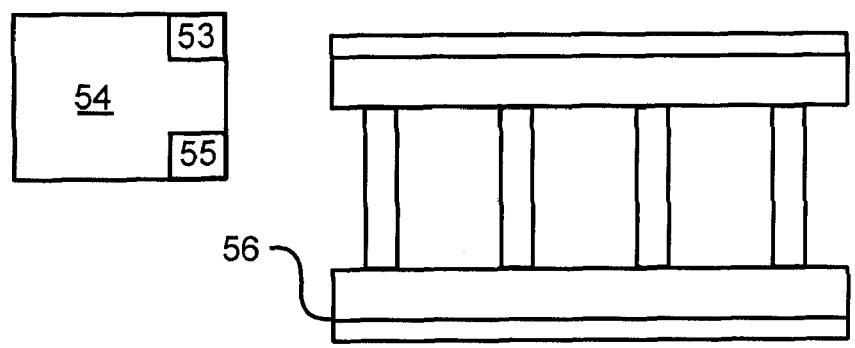
Figure 2:
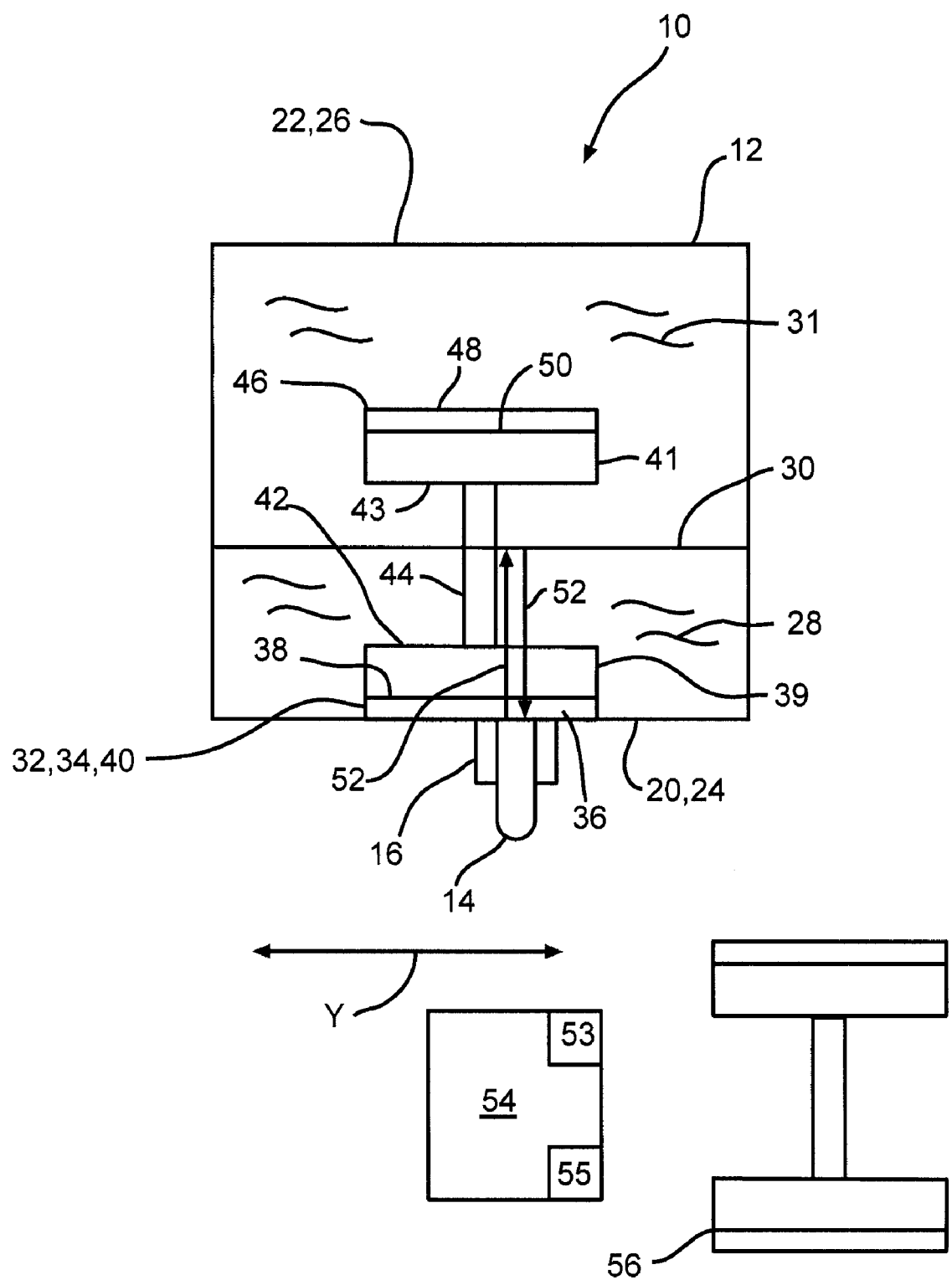
FIG. 2 is a side view of the embodiment of FIG. 1.

FIGS. 1 and 2 depict front and side views of one embodiment of an ultrasonic inspection apparatus 10. The ultrasonic inspection apparatus 10 may comprise a chamber 12, at least one transducer 14, a moveable bubble-shoe 16, and a moving member 18. The chamber 12 may comprise a first portion 20 and a second portion 22. The first portion 20 may comprise a bottom surface 24 of the chamber 12. The bottom surface 24 may be made of Plexiglass, Aluminum, and/or a material through which ultrasonic signals travel well. The second portion 22 may comprise a top surface 26 of the chamber 12.

The chamber 12 may be partly filled with water 28 disposed between the first portion 20 of the chamber 12 and a water-line 30 disposed apart from the second portion 22 of the chamber 12. A gas 31 such as air or another type of gas may be disposed between the water-line 30 and the second portion 22 of the chamber 12. A portion 32 of a part 34 being inspected may be disposed within the water 28 between the first portion 20 of the chamber 12 and the water-line 30. The part 34 may be disposed on the first portion 20 of the chamber 12. The part 34 being inspected may comprise a complex-shaped part such as a floor beam 40. The portion 32 of the part 34 being inspected may comprise a thin gauge bonded spar cap 36 which may be bonded at a bond-line 38 to a first flange 39 of the floor beam 40. The floor beam 40 may comprise the first flange 39 and a second flange 41 each respectively welded to opposing sides 42 and 43 of a web 44. The web 44 and the first and second flanges 39 and 41 may each be made of Titanium and/or another type of metal. The cap 36 may be made of a composite such as Graphite Epoxy. Another portion 46 of the part 34 which is not currently being inspected may be disposed above the water 28 between the water-line 30 and the second portion 22 of the chamber 12. The another portion 46 of the part 34 not currently being inspected may comprise another cap 48 which may be bonded at another bond-line 50 to the second flange 41.

The at least one transducer 14 may be disposed apart from the water-line 30 for emitting ultrasonic signals 52 through the portion 32 of the part 34 being inspected towards the water-line 30. The at least one transducer 14 may comprise a linear array transducer, multiple transducers, a single transducer, and/or another type of transducer. The at least one transducer 14 may be disposed below the first portion 20 of the chamber 12. The at least one transducer 14 may be disposed at least one of against and within a moveable bubble-shoe 16 which may be attached to a moving member 18. The moving member 18 may be adapted to move the at least one transducer 14 and the bubble-shoe 16 to multiple positions relative to the part 34 in order to inspect the entire portion 32 of the part 34. The moving member 18 may comprise a moving bridge and/or another type of mechanical device which is adapted to move the bubble-shoe 16 and the at least one transducer 14 relative to the part 34. The moving member 18 may be adapted to move the bubble-shoe 16 and the at least one transducer 14 in X and/or Y directions.

The at least one transducer 14 may emit ultrasonic signals 52 through the first portion 20 of the chamber 12, through the portion 32 of the part 34 being inspected, and towards the water-line 30. The water-line 30 may reflect the ultrasonic signals 52 off the water-line 30, back through the portion 32 of the part 34 being inspected, and back to the at least one transducer 14. The at least one transducer 14 may receive the reflected ultrasonic signals 52 and send data 53 (i.e. results) regarding the received ultrasonic signals 52 to one or more computers 54. The moving member 18 may move the at least one transducer 14 and the bubble-shoe 16 in X and/or Y directions along the first portion 20 of the chamber 12 relative to the part 34 in order to allow the at least one transducer 14 to emit ultrasonic signals 52 over the entire portion 32 of the part 34 being inspected. The one or more computers 54 may evaluate the data 53 in order to determine a condition of the portion 32 of the part 34 being inspected such as a bond-line 38 in between a cap 36 and a first flange 39 of a floor beam 40. The one or more computers 54 may evaluate the data 53 by comparing it against data 55 gathered during the prior ultrasonic inspection of a standard 56 of the part 34 being inspected. The standard 56 of the part 34 being inspected may comprise a model-part having known anomalies in order to determine the condition of the part 34. After the portion 32 of the part 34 is inspected, the part 34 may be flipped over in the water 28 so that the another portion 46 of the part 34 is below the water-line 30 while the portion 32 of the part 34 is above the water-line 30 in order to inspect the another portion 46 of the part 34. In such manner, various portions of the part 34 may be inspected.

The water-line 30 may be the only surface for reflecting the ultrasonic signals 52 within the chamber 12. By using the water-line 30 as the only reflecting surface, one or more complex parts 34 may be inspected without the need for one or more reflector plates within the chamber 12. This may save money during manufacturing by avoiding the use of extra parts.

Figure 3:
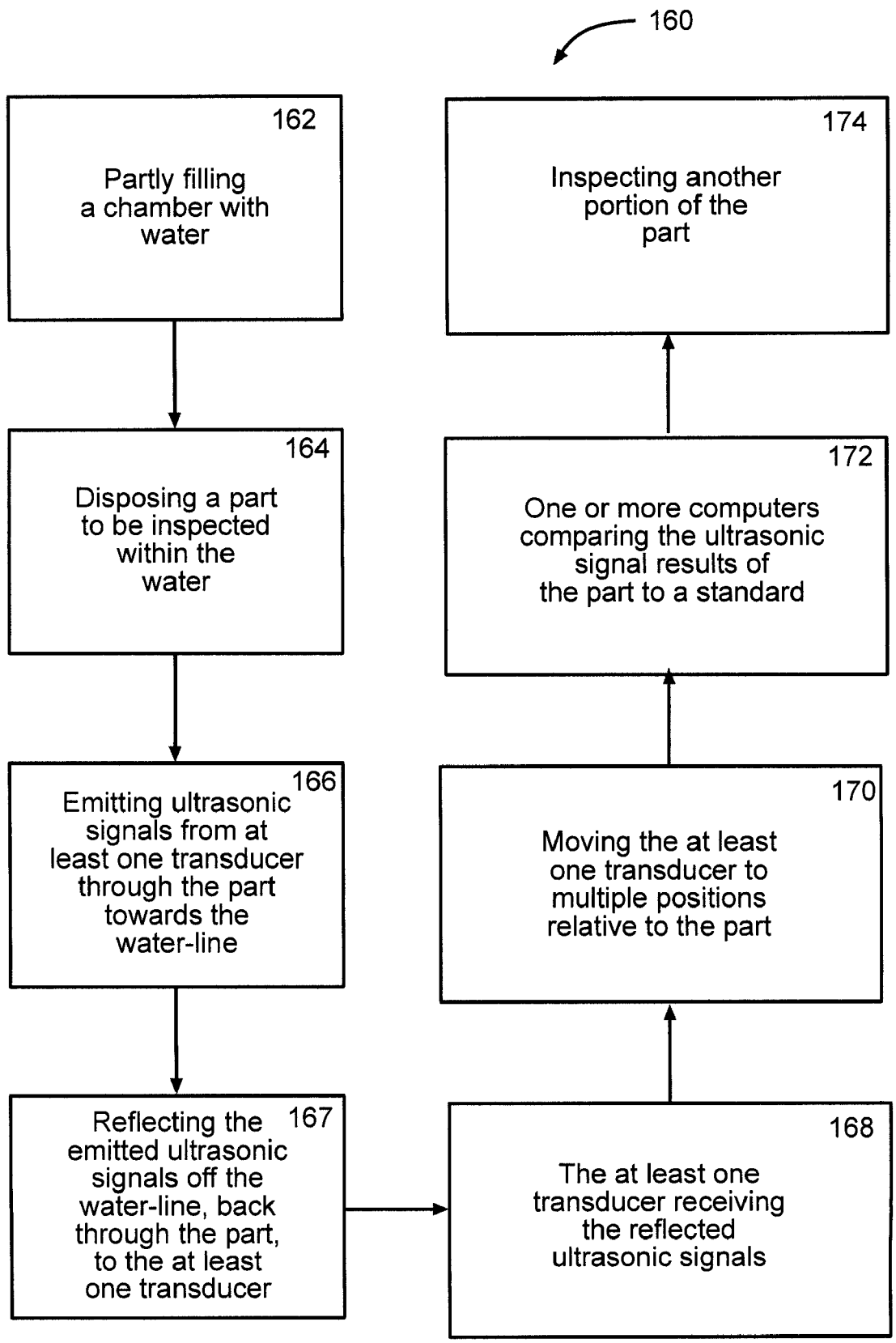
FIG. 3 is a flowchart of one embodiment of a method for inspecting a part.

FIG. 3 is a flowchart of one embodiment of a method 160 for inspecting a part 34. In step 162, a chamber 12 may be partly filled with water 28 from a first portion 20 of the chamber 12 to a water-line 30 disposed apart from a second portion 22 of the chamber 12. The first portion 20 of the chamber 12 may comprise a bottom surface 24 of the chamber 12, and the second portion 22 of the chamber 12 may comprise a top surface 26 of the chamber 12. The bottom surface 24 of the chamber 12 may comprise at least one of Plexiglass, Aluminum, and a material through which ultrasonic signals 52 travel well. Step 162 may comprise disposing and/or leaving a gas such as air between the water-line 30 and the second portion 22 of the chamber 12.

In step 164, a portion 32 of the part 34 to be inspected may be disposed within the water 28 within the chamber 12. Step 164 may comprise disposing the portion 32 of the part 34 being inspected within the water 28 between the first portion 20 of the chamber 12 and the water-line 30. The part 34 being inspected may comprise a complex-shaped part such as a thin gauge bonded spar cap 36 which may be bonded at a bond-line 38 to a first flange 39 of the floor beam 40. The floor beam 40 may comprise the first flange 39 and a second flange 41 each respectively welded to opposing sides 42 and 43 of a web 44. The web 44 and the first and second flanges 39 and 41 may each be made of Titanium and/or another type of metal. The cap 36 may be made of a composite such as Graphite Epoxy.

In step 166, ultrasonic signals 52 may be emitted from at least one transducer 14 through the portion 32 of the part 34 being inspected towards the water-line 30. The at least one transducer 14 may be disposed below the first portion 20 of the chamber 12. The at least one transducer 14 may comprise at least one of a linear array transducer, multiple transducers, a single transducer, and/or another type of transducer. The at least one transducer 14 may be disposed against and/or within a moveable bubble-shoe 16 which may be attached to a moving member 18. In step 167, the emitted ultrasonic signals 52 may be reflected off the water-line 30, back through the portion 32 of the part 34 being inspected, back to the at least one transducer 14. The water-line 30 may be the only surface which reflects the ultrasonic signals 52 emitted from the at least one transducer 14, and the chamber 12 may not contain any reflector plates.

In step 168, the at least one transducer 14 may receive the reflected ultrasonic signals 52. In step 170, the at least one transducer 14 may be moved, using the moving member 18, to multiple positions relative to the part 34 being inspected in order to inspect the entire portion 32 of the part 34. In such manner, the entire bond-line 38 between the first flange 39 and the cap 36 may be inspected. In step 172, one or more computers 54 may compare data 53 (i.e. ultrasonic inspection results) regarding the received ultrasonic signals 52 against prior ultrasonic inspection results/data 55 of a standard 56 of the part 34 in order to determine a condition of the part 34 being inspected, such as the condition of a bond-line 38 in between a cap 36 and a first flange 39 of a floor beam 40. The standard 56 of the part 34 inspected may comprise a model-part having known anomalies in order to determine the condition of the part 34.

In step 174, after the portion 32 of the part 34 is inspected, the part 34 may be flipped over in the water 28 so that the another portion 46 of the part 34 is below the water-line 30 while the portion 32 of the part 34 is above the water-line 30 in order to inspect the another portion 46 of the part 34. In such manner, various portions of the part 34 may be inspected.

The use of one or more of the disclosed embodiments utilizing a water-line 30 as a reflector of ultrasonic signals 52 in order to inspect a portion 32 of a part 34 may be more accurate and consistent than conventional pulse echo ultrasound techniques, and may be less expensive and/or time-consuming than conventional reflector plate pulse-echo ultrasonic testing which may require the use of specific tooling for each part being inspected.

It should be understood, of course, that the foregoing relates to exemplary embodiments of the disclosure and that modifications may be made without departing from the spirit and scope of the disclosure as set forth in the following claims.

We claim:

1. An ultrasonic inspection apparatus comprising:
   a chamber partly filled with water from a first portion of the chamber to a water-line disposed apart from a second portion of the chamber; and
   at least one transducer disposed apart from the water-line for emitting ultrasonic signals through a portion of a part being inspected towards the water-line;
   wherein the water-line is for reflecting the ultrasonic signals emitted from the at least one transducer off the water-line, back through a portion of a part being inspected, and back to said at least one transducer.

2. The ultrasonic inspection apparatus of claim 1 wherein gas or air is disposed between the water-line and the second portion of the chamber.

3. The ultrasonic inspection apparatus of claim 1 wherein the first portion of the chamber comprises a bottom surface of the chamber and the second portion of the chamber comprises a top surface of the chamber.

4. The ultrasonic inspection apparatus of claim 3 wherein the bottom surface of the chamber comprises Plexiglass, Aluminum, or a material through which ultrasonic signals travel well.

5. The ultrasonic inspection apparatus of claim 3 wherein said at least one transducer is disposed entirely below the bottom surface of the chamber.

6. The ultrasonic inspection apparatus of claim 1 wherein said at least one transducer comprises a linear array transducer, multiple transducers, or a single transducer.

7. The ultrasonic inspection apparatus of claim 1 wherein said at least one transducer is disposed against or within a moveable bubble-shoe and said at least one transducer is attached to a moving member for moving the transducer to multiple positions relative to the part being inspected.

8. The ultrasonic inspection apparatus of claim 1 wherein the part comprises a thin gauge bonded spar cap.

9. The ultrasonic inspection apparatus of claim 8 wherein the thin gauge bonded spar cap is bonded to a first flange of a floor beam, and the ultrasonic inspection apparatus is for inspecting a bond-line between the spar cap and the first flange.

10. The ultrasonic inspection apparatus of claim 1 wherein the portion of the part being inspected is disposed within the water between the first portion of the chamber and the water-line.

11. The ultrasonic inspection apparatus of claim 1 wherein there is no reflector plate and the water-line is the only surface for reflecting the ultrasonic signals emitted from the at least one transducer.

12. The ultrasonic inspection apparatus of claim 1 further comprising a standard of the part being inspected for comparison of ultrasonic inspection results of the standard relative to ultrasonic inspection results of the part being inspected.

13. The ultrasonic inspection apparatus of claim 1 wherein the first and second portions comprise opposed inner surfaces of the chamber, and gas or air is disposed between the water-line and the second portion of the chamber.

14. The ultrasonic inspection apparatus of claim 13 wherein the first portion comprises a bottom inner surface of the chamber and the second portion comprises a top inner surface of the chamber.

15. A method for inspecting a part comprising:
   filling a chamber partly with water from a first portion of the chamber to a water-line disposed apart from a second portion of the chamber;
   disposing a portion of a part to be inspected within the water within the chamber;
   emitting ultrasonic signals from at least one transducer through the portion of the part being inspected towards the water-line; and
   reflecting the emitted ultrasonic signals off the water-line, back through the portion of the part being inspected, back to the at least one transducer.

16. The method of claim 15 wherein the filling step further comprises disposing gas or air between the water-line and the second portion of the chamber.

17. The method of claim 15 wherein the first portion of the chamber comprises a bottom surface of the chamber and the second portion of the chamber comprises a top surface of the chamber.

18. The method of claim 17 wherein the bottom surface of the chamber comprises Plexiglass, Aluminum, or a material through which ultrasonic signals travel well.

19. The method of claim 17 wherein said at least one transducer is disposed entirely below the bottom surface of the chamber.

20. The method of claim 15 wherein said at least one transducer comprises a linear array transducer, multiple transducers, or a single transducer.

21. The method of claim 15 wherein said at least one transducer is disposed against or within a moveable bubble-shoe, and further comprising moving said at least one transducer, using a moving member, to multiple positions relative to the part being inspected.

22. The method of claim 15 wherein the part being inspected comprises a thin gauge bonded spar cap.

23. The method of claim 22 wherein the thin gauge bonded spar cap is bonded to a first flange of a floor beam, and further comprising inspecting a bond-line between the spar cap and the first flange.

24. The method of claim 15 wherein the disposing step comprises disposing the portion of the part being inspected within the water between the first portion of the chamber and the water-line.

25. The method of claim 15 wherein the water-line is the only surface which reflects the ultrasonic signals emitted from the at least one transducer and there is no reflector plate.

26. The method of claim 15 further comprising the step of comparing ultrasonic inspection results of the part being inspected against ultrasonic inspection results of a standard of the part in order to determine a condition of the part being inspected.

27. The method of claim 15 wherein the first and second portions comprise opposed inner surfaces of the chamber, and wherein the filling step further comprises inserting at least one of gas or air between the water-line and the second portion of the chamber.

28. The method of claim 27 wherein the first portion comprises a bottom inner surface of the chamber and the second portion comprises a top inner surface of the chamber.

* * * * *